United States Patent [19]

Moritz

[11] Patent Number: 4,864,844

[45] Date of Patent: Sep. 12, 1989

[54] METHOD AND APPARATUS FOR EVALUATING CONDENSATION AMOUNT

[75] Inventor: Robert R. Moritz, Riverdale, Ga.

[73] Assignee: Rolls-Royce plc, Greenwich, Conn.

[21] Appl. No.: 945,461

[22] Filed: Dec. 23, 1986

[51] Int. Cl.$^4$ .............................................. G01N 7/00
[52] U.S. Cl. ............................................ 73/29; 73/335
[58] Field of Search ...................... 73/29, 335, 338, 23

[56] References Cited

U.S. PATENT DOCUMENTS

| | | | |
|---|---|---|---|
| 3,234,780 | 2/1966 | Pappas | 73/29 |
| 3,738,154 | 6/1973 | Henry | 73/19 |
| 4,028,942 | 6/1977 | Gardiner | 73/335 |
| 4,507,875 | 4/1985 | Hirsch et al. | 73/29 |

FOREIGN PATENT DOCUMENTS 767337  1/1957  United Kingdom ..................... 73/29

Primary Examiner—Hezron E. Williams
Attorney, Agent, or Firm—Cushman, Darby & Cushman

[57] ABSTRACT

In order to evaluate the condensation amount in a jet engine intake duct, for calibrating the engine, apparatus are provided which induce a high speed flow of air through a duct. The duct is designed so that the air velocity within it very gradually increases along it until a choked (sonic) condition is reached. At or around sonic conditions static pressure is very responsive to changes in flow due to condensation. Thus by first obtaining a pressure profile along the duct under non-condensing conditions and then comparing this with a pressure profile under condensing conditions a condensation amount can be computed.

12 Claims, 1 Drawing Sheet

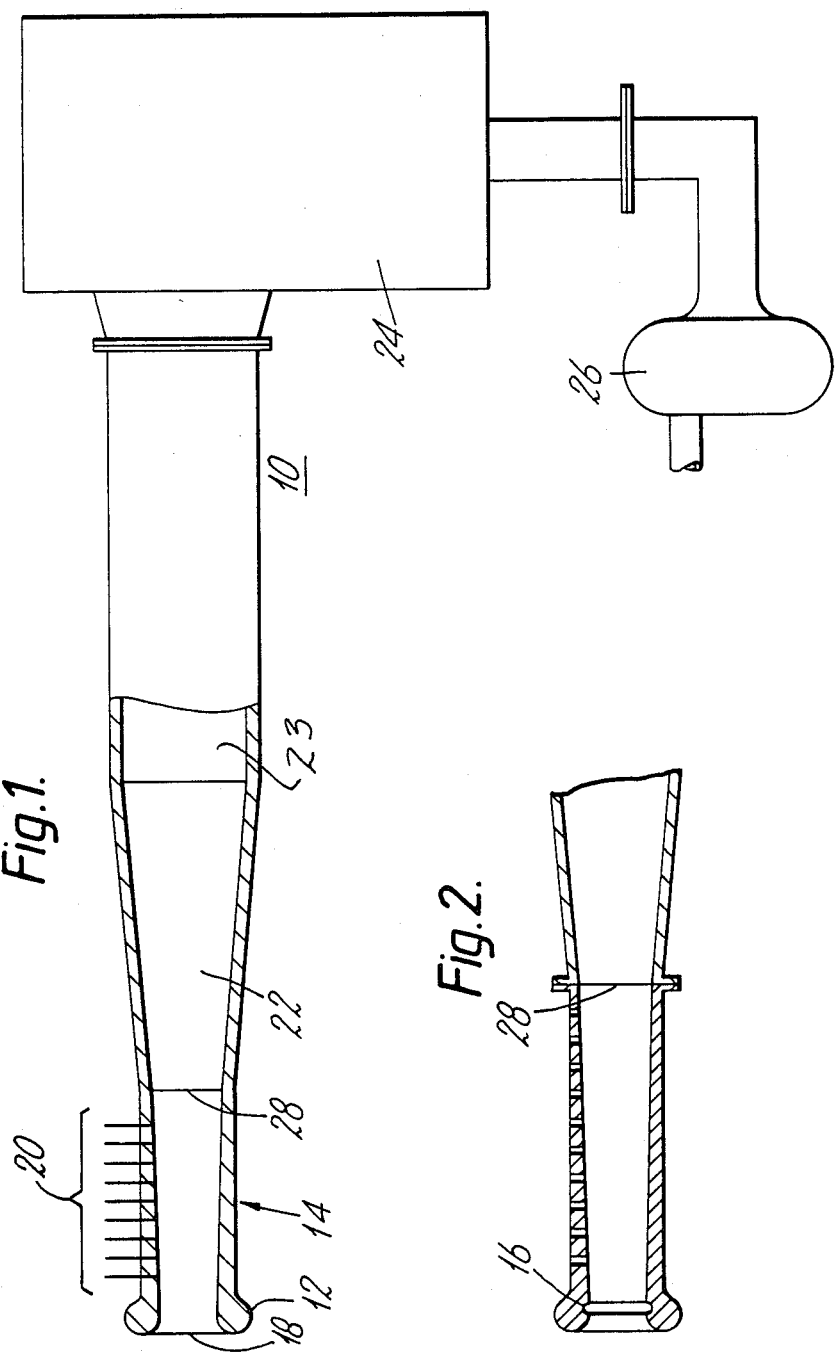

METHOD AND APPARATUS FOR EVALUATING CONDENSATION AMOUNT

BACKGROUND OF INVENTION

Field of Invention

The present invention relates to a method and apparatus for measuring the condensation amount in a flow of gas.

A seasonal variation in recorded performance of consistently constructed aircraft jet engines, together with variable amounts of condensate occurring in the engine intake apparatus during calibration, gives rise to a requirement to quantify the amount of water condensing in the intake apparatus. Condensation and subsequent re-evaporation in other parts of the engine is expected to affect the engine thermal cycle (by raising the temperature at which compression takes place) and other physical processes relating to the condensed fluid. Therefore condensation would appear to explain the seasonal variation in performance during engine calibration due to changing atmospheric conditions.

Condensation arises in the engine intake apparatus because of the high induced velocity causing a depressed air temperature as it enters the engine intake. The water content of the air, however, remains unchanged thereby increasing the relative humidity. With the high induced air velocity encountered on modern intakes the relative humidity may rise above 100% on some test occasions causing condensation and slightly decreasing the amount of temperature depression relative to simple dry air theory.

Condensation is not readily measured directly and is not open to reliable prediction without obtaining data concerning the numerical, physical and chemical composition of the local atmosphere. A new approach is therefore required.

SUMMARY OF THE INVENTION

An object of the invention is to provide a method for measuring the amount of condensation in a flow of gas containing a vapor.

Another object of the invention is to provide apparatus for use in the above method.

In accordance with the present invention dry air is first induced through a tapered duct with gradually increasing velocity until sonic velocity is reached. A static pressure 'reference' profile is then obtained under non-condensing conditions with dry gas. Then a pressure profile under condensing conditions is obtained and compared with the reference profile to obtain a condensation amount.

In accordance with a further aspect of the invention apparatus for use in the above-mentioned method comprises a tapered duct provided with at least one static pressure gauges and means for inducing a flow through the duct.

BRIEF DESCRIPTION OF DRAWINGS

FIG. 1 shows apparatus according to one aspect of the present invention.

FIG. 2 depicts in more detail part of the apparatus in FIG. 1.

DESCRIPTION OF PREFERRED EMBODIMENT

The apparatus 10 comprise a small intake flare 12 of about 1" diameter (throat) upstream of a nearly parallel duct 14 of approximately 1' length. The duct 14 tapers by about 0.050" diameter per foot length to almost balance the increasing displacement thickness of developing wall boundary layers, and is provided with circumferential grooves 16 at its inlet 18 to ensure a consistent forced boundary layer transition at this point. The duct 14 has a a plurality of static pressure gauges 20 so that the development of pressure along the duct 14 can be measured.

Downstream of the near parallel duct 14 and upstream of a parallel duct 23, a diffuser, section 22 by reducing the pressure ratio of the flow is provided for energy conservation. A plenum chamber 24 is situated in flow series between the diffuser 22 and a pump 26.

The nearly parallel duct 14 is designed to maintain a very slightly increasing velocity from inlet 18 to exit 28. Thus when the pump 26 is run, atmospheric air is induced into the duct 14 and becomes sonic around the exit 28. Because of the very gradual increase in air velocity along the duct 14, the air is very close to sonic velocity throughout its length. At or near sonic conditions the local air pressure is extremely responsive to flow changes resulting from condensation. In particular the total/static pressure ratio $$\left(\frac{P_t}{P}\right) = \left\{1 + \frac{(\gamma - 1)}{2} M_n^2\right\}^{\gamma/\gamma - 1} = 1$$

is a continuously rising function of Mach number ($M_n$) through sonic conditions.

Also the flow function $$Q = \frac{M\sqrt{T}}{A \times P_t} = 2$$

Where

| | |
|---|---|
| M = mass flow rate | $\rho$ = density |
| $T_t$ = total temperature | C = velocity |
| A = area | R = gas constant |
| $P_t$ = total pressure | |
| $\gamma$ = ratio of specific heats | | substituting equation 1 into equation 2 and using the expressions $$M = \rho AC \text{ where } \rho = \frac{P}{RT} \text{ and } -Mn = \frac{C}{\sqrt{\gamma RT}} = \frac{C}{\gamma \sqrt{gRT}}$$

then $$Q = \frac{M_n \sqrt{\gamma g/R}}{\sqrt{\left\{1 + \frac{(\gamma - 1)}{2} M_n^2\right\}^{\frac{\gamma+1}{\gamma-1}}}} = 3$$

Since Q is a maximum when $M_n 1.0$ it follows that $d(P_t/P)/dQ$ is infinite at $M_n = 1.0$ for a perfect gas.

The process of condensation directly raises total temperature and at transonic Mach number drops the total pressure (due to heat exchange with the working fluid) and the effective mass flow ($T_t$ and $P_t$ terms dominate however) as the water phase changes. At transonic velocities small changes in Q along the duct result in large changes in $P_t/P$. A more rigorous evaluation would involve taking into account changes in $\gamma$ and $\rho$ etc.

In operation the apparatus is first run using dry air so that a non-condensing reference pressure profile along the duct 14 can be obtained. The effective area at any position along the duct can be estimated with the aid of 'Stratford and Beavers Boundary layer Calculation' (HMSO R and M 3207). This boundary layer assessment is assumed correct for the dry air test by regarding total pressure as constant. The calculated boundary layer thickness then allows for the geometrical duct area to be corrected to effective duct area. With the total pressure in the mainstream constant, the Mach number at each static pressure gauge tapping can be calculated.

The continuity of mass flow along the duct can then be checked and any small errors used as a trim factor to determine a final effective duct area at each pressure tapping. There may be some error due to theoretical imperfection and irregularities in static tapping hole shape.

Next, a condensing pressure profile is obtained using 'wet' air and using the calibrated effective areas. Any further continuity errors are assumed to be caused by condensation.

The amount of condensation is calculated by way of guessing a condensation amount which is known to release a given amount of heat (from the latent heat of vaporisation of water). Thus, from a given amount of heat released (dM) the associated change in total temperature and total pressure in a fixed area duct can be derived from Rayleigh flow assumptions. i.e.

$$dM = (\rho(T_2 - T_1) + \tfrac{1}{2}(C_2^2 - C_1^2)$$

where $T_1$ and $T_2$ are initial and subsequent temperatures, and $C_1$ and $C_2$ are initial and subsequent velocities.

A minor problem is that compressible flow down a duct behaves differently when a thick boundary layer is present. In particular the local speed of sound does not equal $$\sqrt{\gamma RT} \ .$$

A rather primitive allowance is made for this but an elegant solution is not available.

Once change in total temperature and pressure are evaluated then using equation 2 variation in the flow function, Q, and variation in apparent Mach number along the duct (equation 3) are evaluated. Using equation 1 and the static pressure readings obtained under condensing conditions a set of actual Mach number development along the duct can be obtained. If the apparent and actual Mach number readings are the same then the guessed amount of condensation must be correct. If not the condensation amount is varied and the calculation is repeated.

Accurate calculations also have to take into account changes in effective duct area and gas 'constants'. From results obtained so far a 1psi average wall pressure change results from a 15° C. condensation temperature rise.

For comparison with an actual engine intake duct, providing the duct Mach number is not much above 1.0 a short length of sonic duct gives variable amounts of condensation of similar character to an engine (ie hetrogenous nucleation particle dependant rather than homogeneous). The engine duct condensation can then be predicted from the particle condensation evaluated from the apparatus.

It has been found that the apparatus can be used at Mach numbers as low as 0.8 at a penalty of reduced sensitivity and/or in increased duct length. It has been found that an intake flow straightening section is required with Mach numbers of 0.8 to suppress pressure variations arising from atmospheric turbulence which otherwise would disguise condensation related pressure changes.

I claim:

1. Apparatus for measuring the amount of condensation in a flow of gas containing a vapour comprising a near parallel duct which includes a gradually tapering internal flow section adapted to gradually accelerate the gas and vapor to a sonic velocity, means for causing the gas and vapor to flow through the duct and at least one static pressure gauge adapted to measure the static pressure in the duct when the apparatus is used both under condensing and non-condensing conditions whereby comparison of the measured static pressure is used to calculate a condensation amount.

2. Apparatus as claimed in claim 1s wherein there are a plurality of static pressure gauges situated at intervals along the duct adapted to measure static pressure distribution along the duct.

3. Apparatus as claimed in claim 1 wherein a small intake flare is provided at an upstream end of the duct together with a circumferentially extending groove positioned at an upstream entrance to the duct.

4. Apparatus as claimed in claim 1 further comprising a diffuser section downstream of the duct and a plenum chamber situated between the diffuser and the means for causing a flow through the duct.

5. Apparatus as claimed in claim 1 wherein the means for causing a flow through the duct comprises a pump of sufficient flow capacity to induce a transonic flow velocity in the duct.

6. Apparatus as claimed in claim 1 wherein the duct tapers to cause the flow velocity to gradually increase in a downstream direction.

7. A method of measuring the amount of condensation in flow of gas containing a vapor comprising the steps of:

inducing and maintaining a flow of dry gas through a tapered duct shaped to accelerate the flow to a sonic velocity and measuring the development of static pressure along the duct, and then inducing and maintaining a flow of gas and vapor through the same duct and measuring the static pressure along the duct in which condensation is occurring comparing the change in pressure along the duct due to condensation to evaluate the condensation amount using known continuity gas equations.

8. A method as claimed in claim 7 wherein the amount of condensation is iteratively calculated by first using a first amount of condensation, corresponding to a guessed amount, which causes a known change in total pressure and temperatures in a fixed area duct to calculate an apparent Mach number variation in the duct and then comparing this with the actual Mach number variation calculated from the measurement of static pressure in the duct under condensing conditions and repeating the comparison with varying amounts of condensation until the apparent Mach number variation and the actual Mach number variation in the duct substantially agree wherein the guessed amount of condensation corresponding with the apparent Mach number is the actual amount of condemsation occuring in the duct.

9. A method as claimed in claim 7 wherein the gas is air containing water vapor.

10. Apparatus for measuring the amount of condensation in a flow of gas containing a vapor, comprising a near parallel duct which includes a gradually tapering internal flow section adapted to gradually accelerate the gas and vapor, the duct having a small intake vapor provided at an upstream end of the duct and a circumferentially extending groove positioned at an upstream entrance to the duct:

means for causing the gas and vapor to flow through the duct;

and at least one static pressure gauge adapted to measure the static pressure in the duct when the apparatus is used both under condensing and non-condensing conditions whereby comparison of the measured static pressure is used to calculate the condensation amount.

11. Apparatus for measuring the amount of condensation in a flow of gas containing a vapor, comprising a near parallel duct which includes a gradually tapering internal flow section adapted to gradually accelerate the gas and vapor:

means for causing the gas and vapor to flow through the duct;

at least one static pressure gauge adapted to measure the static pressure in the duct when the apparatus is used both under condensing and non-condensing conditions whereby comparison of the measured static pressure is used to calculate a condensation amount;

a diffuser section positioned downstream of the duct; and a plenum chamber situated between a diffuser and the means for causing a flow through the duct.

12. A method of measuring the amount of condensation in a flow of gas containing a vapor comprising the steps of:

inducing and maintaining a flow of dry gas through a tapered duct and measuring the development of static pressure along the duct, inducing and maintaining a flow of gas and vapor through the same duct and measuring the static pressure along the duct in which condensation is occurring, comparing the change in pressure along the duct due to condensation, and calculating the amount of condensation, by using a first amount of condensation corresponding to a guessed amount, which causes a known change and total pressure and temperature in a fixed area duct to calculate an apparent Mach number variation in the duct and then comparing with the actual Mach number variation calculated from the measurement of static pressure in the duct under condensing conditions and repeating the comparison with varying amounts of condensation until the apparent mach number variation and the actual Mach number variation in the duct substantially agree wherein the guessed amount of condensation corresponding with the apparent Mach number is the actual amount of condensation occurring in the duct.

* * * * *

UNITED STATES PATENT AND TRADEMARK OFFICE
CERTIFICATE OF CORRECTION

PATENT NO. : 4,864,844

DATED : September 12, 1989

INVENTOR(S) : Moritz

It is certified that error appears in the above-identified patent and that said Letters Patent is hereby corrected as shown below:

On the title page, item [73], should read
--[73] Assignee: ROLLS-ROYCE INC., Greenwich, Conn.--.

Column 2, line 10, after "22" please insert --, is provided for energy conservation--;

lines 11 and 12, delete "is provided for energy conservation--;

line 25, change "=" to --Equation--;

line 35, change "M" to --$\dot{M}$--; and change "T" to --$T_t$--; and change "=" to --Equation--;

line 40, change "M" to --$\dot{M}$--;

line 50, change "M" to --$\dot{M}$--; and after "and" delete the dash;

line 55, change "=" to --Equation--;

line 61, change "$M_n$ 1.0" to --$M_n = 1.0$--.

UNITED STATES PATENT AND TRADEMARK OFFICE
CERTIFICATE OF CORRECTION

PATENT NO. : 4,864,844

DATED : September 12, 1989

INVENTOR(S) : Moritz

It is certified that error appears in the above-identified patent and that said Letters Patent is hereby corrected as shown below:

Column 3, line 3, change "/" to --C/--;

line 10, change "and" to --&--;

line 35, change "(" to --C--.

Signed and Sealed this

Nineteenth Day of March, 1991

*Attest:*

HARRY F. MANBECK, JR.

*Attesting Officer*  *Commissioner of Patents and Trademarks*